United States Patent
Brunner et al.

(10) Patent No.: US 9,086,413 B2
(45) Date of Patent: Jul. 21, 2015

(54) METHODS OF PREDICTING CLINICAL OUTCOME IN MALIGNANT MELANOMA

(76) Inventors: Georg Brunner, Telgte (DE); Jens Atzpodien, Munster (DE)

( * ) Notice: Subject to any disclaimer, the term of this patent is extended or adjusted under 35 U.S.C. 154(b) by 524 days.

(21) Appl. No.: 13/381,284

(22) PCT Filed: Jun. 29, 2009

(86) PCT No.: PCT/EP2009/004673
§ 371 (c)(1),
(2), (4) Date: Dec. 28, 2011

(87) PCT Pub. No.: WO2011/000388
PCT Pub. Date: Jan. 6, 2011

(65) Prior Publication Data
US 2012/0108447 A1 May 3, 2012

(51) Int. Cl.
*C12Q 1/68* (2006.01)
*G01N 33/574* (2006.01)
*C12N 15/10* (2006.01)

(52) U.S. Cl.
CPC ........ *G01N 33/5743* (2013.01); *C12N 15/1096* (2013.01); *G01N 2800/52* (2013.01)

(58) Field of Classification Search
None
See application file for complete search history.

(56) References Cited

FOREIGN PATENT DOCUMENTS

WO    WO 2008/031041 A2    3/2008
WO    WO 2008/141275 A1    11/2008

OTHER PUBLICATIONS

Bittner et al., *Molecular classification of cutaneous malignant melanoma by gene expression profiling*, Nature, Aug. 2000, vol. 406, pp. 536-540.
Brunner et al., *Increased Expression of the Tumor Suppressor PLZF Is a Continuous Predictor of Long-Term Survival in Malignant Melanoma Patients*, Cancer Biotherapy & Radiopharm., 2008, vol. 23(4):451-459.
Jaeger et al., *Gene Expression Signatures for Tumor Progression, Tumor Subtype, and Tumor Thickness in Laser-Microdissected Melanoma Tissues*, Clin Cancer, Feb. 2007:13(3), pp. 806-815.
Riker et al., *The gene expression profiles of primary and metastatic melanoma yields a transition point of tumor progression and metastasis*, BMC Medical Genomics, Apr. 2008, 1:13.
Winnepenninckx et al., *Gene Expression Profiling of Primary Cutaneous Melanoma and Clinical Outcome*, Natl Cancer Inst, Apr. 2006, vol. 98, No. 7, pp. 472-482.
Alonso et al., *A High-Throughput Study in Melanoma Identifies Epithelial-Mesenchymal Transition as a Major Determinant of Metastasis*, Cancer Res, Apr. 2007, 67:(7), pp. 3450-3460.
Smith et al., *Whole-Genome Expression Profiling of the Melanoma Progression Pathway Reveals Marked Molecular Differences between Nevi/Melanoma In Situ and Advanced-Stage Melanomas*, Cancer Biology and Ther., Sep. 2005, vol. 4(9), pp. 1018-1029.
Katoh et al., *Integrative genomic analyses on HES/HEY family: Notch-independent HES1, HES3 transcription in undifferentiated ES cells, and Notch-dependent HES1, HES5, HEY1, HEY2, HEYL transcription in fetal tissues, adult tissues, or cancer*, Int. J. Oncol. 31, 2007, pp. 461-466.
Ren et al., *The Impact of Genomics in Understanding Human Melanoma Progression and Metastasis*, Cancer Control, Jul. 2008, vol. 15, No. 3, pp. 202-215.
Reis et al., *Keratin 9 gene mutations in epidermolytic palmoplantar keratoderma (EPPK)*, Nature Genetics, Feb. 1994, vol. 6, pp. 174-179.
Xiying Yu et al., *SPINK7 (serine peptidase inhibitor, Kazal type 7 (putative))*, Atlas Genet Cytogenet Oncol Haematol 2007, 11:4, pp. 9-11.

*Primary Examiner* — Jim Ketter
(74) *Attorney, Agent, or Firm* — Wolf, Greenfield & Sacks, P.C.

(57) ABSTRACT

Malignant melanoma is the most aggressive type of skin cancer and currently accounts for more than 160.000 new cancer cases worldwide every year. Incidence of malignant melanoma is rapidly increasing—with a doubling rate of 10-20 years and a death rate of 11%. The inventors of the present application found genes that predict overall survival of patients with malignant melanoma and that contain prognostic information not comprised in the conventional histopathological and clinical criteria. Accordingly, the present invention relates to the field of oncology, more particularly to methods of predicting clinical outcome in malignant melanoma as defined in the claims.

15 Claims, 3 Drawing Sheets

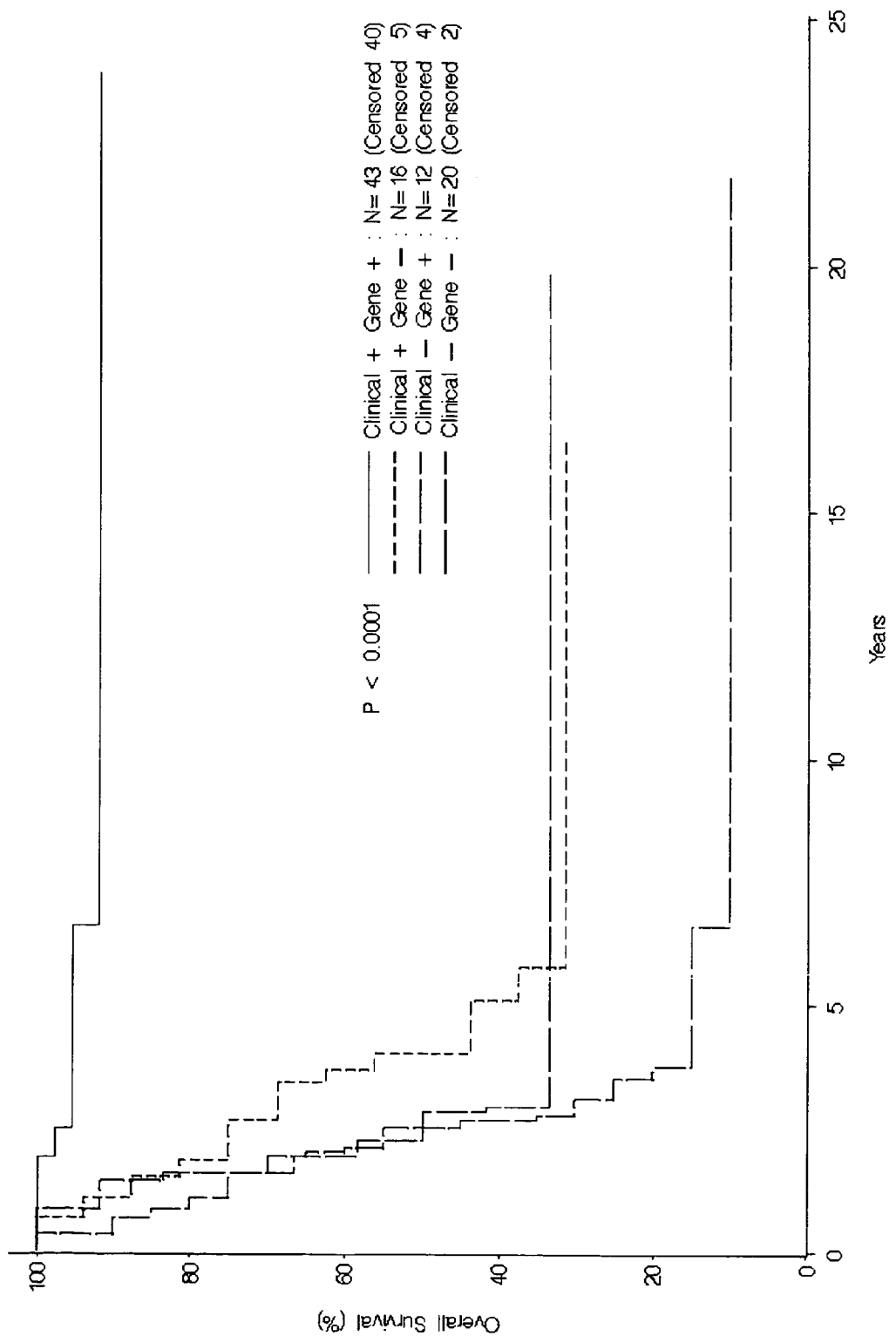

METHODS OF PREDICTING CLINICAL OUTCOME IN MALIGNANT MELANOMA

RELATED APPLICATIONS

This application is a national stage filing under 35 U.S.C. §371 of international application, PCT/EP2009/004673 filed Jun. 29, 2009, designating the United States of America, and which was published in English under PCT Article 21(2).

FIELD OF THE INVENTION

The present invention relates to the field of oncology, more particularly to methods of predicting clinical outcome in malignant melanoma. Malignant melanoma is the most aggressive type of skin cancer and currently accounts for more than 160.000 new cancer cases worldwide every year. Incidence of malignant melanoma is rapidly increasing—with a doubling rate of 10-20 years and a death rate of 11%. However, the molecular mechanisms underlying melanoma progression are largely unknown, and target-specific therapies are lacking. The currently used TNM (tumor, node, metastasis)-based staging system of the American Joint Committee on Cancer (AJCC), comprising histopathological and clinical criteria such as Breslow tumor thickness, lymph node status, and ulceration, is inadequate to provide a precise prognosis for all patients.

Gene signatures associated with cancer malignancy, derived from expression profiling studies using DNA microarray analysis or reverse-transcriptase polymerase chain reaction (RT-PCR), have developed into a valuable tool in tumor classification and prognosis, particularly in breast cancer. Moreover, molecular signatures are not only useful for cancer classification into clinically relevant subtypes and for predicting disease recurrence and response to treatment, they might also have an impact on future patient management.

Gene expression profiling has been successfully used to define new subtypes (Bittner et al., 2000; Jaeger et al., 2007) as well as stage-specific genetic markers (Riker et al., 2008; Jaeger et al., 2007) in cutaneous melanoma. In this context, Jaeger et al. mentions SCGB2A2 in a list of 332 genes downregulated in melanoma metastases tissues as compared to primary melanomas. However, the authors rather focus on other genes as being significantly predictive. Furthermore, Riker et al. mentions HES6 and COL6A6 being also differentially expressed in melanoma tissue. Noteworthy, Riker et al. disclose that HES6 is part of a group of 92 genes which are downregulated in primary melanoma tissue as compared to normal human melanocytes, whereas it is shown in the present invention that HES6 is being upregulated again in metastatic primary melanoma tissue as compared to non-metastatic primary melanoma tissue. COL6A6 (previously termed LOC131873) was found to be part of a large group of 1.310 genes which are downregulated in melanoma metastases as compared to primary melanomas.

Gene signatures correlating with clinical outcome are rare and not generally established in malignant melanoma because of the scarcity of large collections of frozen primary tumor specimens associated with clinical follow-up data. Moreover, conventional histopathological and clinical staging criteria are inadequate for reliably predicting the clinical outcome of malignant melanoma, and complementary molecular prognostic markers are not available.

A reliable prediction has potentially important implications for the future development of melanoma therapy. Currently, following first diagnosis and tumor resection, stage IB/II/III patients often receive α-interferon-based protocols irrespective of the individual prognosis. Hence, within this group, a large proportion of good-prognosis patients are treated in the absence of therapeutic need or benefit. Based on reliable outcome prediction, patients at lowest risk may eventually circumvent long-term adjuvant therapy and its toxicity. On the other hand, patients at highest risk may seek additional new treatment options beyond today's standard care.

In primary melanomas, a gene expression profiling study by Winnepenninckx et al. (J. Natl Cancer Inst.; 2006) (on behalf of the Melanoma Group of the European Organization for Research and Treatment of Cancer [EORTC]) identified a set of 254 genes, whose expression was associated with disease-free survival in a cohort of 58 patients (minimum follow-up of four years). This 254-gene classifier was validated using an additional 17 primary melanomas. While none of the genes of the gene signature of the present invention are mentioned in this list of differentially expressed genes (254-gene classifier), three of the genes of the gene signature are mentioned in a list of 652 genes correlating with the thickness of primary melanomas (Supplementary Table 2 of Winnepenninckx et al.). Winnepenninckx et al. focus on other genes than the ones disclosed in the gene signature of the present invention. For example, additional immunohistochemical validation of part of these genes, using paraffin-embedded tissue samples, revealed that two related genes, MCM4 and MCM6, were associated with overall survival, independently of conventional staging parameters.

Another gene expression profiling study reported by Alonso et al. (Cancer Res.; 2007) indicated that expression of genes involved in epithelial-mesenchymal transition (EMT) was associated with disease-free survival in a cohort of 34 melanoma patients (minimum follow-up of three years). Immunohistochemical validation on tissue microarrays identified protein kinase Cα to correlate significantly with disease-free survival, independently of Breslow tumor thickness.

WO 2008/031041 discloses a method of evaluating a melanoma from a patient. In this context, it is disclosed a list of 983 genes whose expression is decreased in metastatic melanoma. Among these genes are DCD, COL6A6 (previously termed LOC131873), and SCGB2A2.

Smith et al. (Cancer Biol. Ther., 2005) mentions DCD, SCGB1D2, SCGB2A2 and PIP in a list of 50 genes being downregulated in advanced-stage melanomas.

Katoh and Katoh (Int. J. Oncol., 2007) note that HES6 is expressed in different types of tumor, inter alia melanoma.

Finally, Ren et al. disclose that HES6 expression correlates with tumor thickness (part of a list of 50 genes), whereas PIP is downregulated during tumor progression from the group of normal skin/nevi/in situ melanomas/radial-growth phase melanomas to the group of vertical-growth phase melanomas/melanoma metastases (part of a group of 77 genes) and SCGB2A2 during progression from primary melanomas to melanoma metastases (part of a group of 181 genes).

However, in all these documents, no statistical correlation to long-term survival and clinical outcome has been drawn.

Accordingly, there still exists a need for providing methods of predicting clinical outcome in malignant melanoma.

SUMMARY OF THE INVENTION

Surprisingly, the inventors found genes that predict overall survival of patients with malignant melanoma and that contain prognostic information not comprised in the conventional histopathological and clinical criteria.

DETAILED DESCRIPTION OF THE INVENTION

As shown in the examples, the inventors have performed a gene expression profiling study with the largest cohort of melanoma patients (136 patients) and with the longest follow-up (up to 286 months) studied so far. Based on their previous gene expression profiling studies, the inventors selected 92 genes and quantified their expression in frozen tissue specimens in a training set of 38 selected high-risk or low-risk primary melanomas, using real-time reverse-transcriptase polymerase chain reaction (RT-PCR) on TaqMan Arrays. mRNA copy numbers were estimated from the cycle threshold (Ct) with the assumptions made that, ideally, efficiency of reverse transcription and real-time PCR were uniform among different samples and that a single mRNA copy yields a Ct of 36 (on TaqMan Arrays). mRNA copy numbers were normalized to µg of total tumor RNA. Gene expression of 11 of the 92 analyzed genes significantly correlated with the overall survival in Cox univariate regression analysis (minimum follow-up of five years) of 38 selected high-risk or low-risk melanoma patients. In order to identify a gene signature that is correlated with the clinical outcome and is independent of conventional staging parameters, expression of these candidate genes was further analyzed in a second step of real-time RT-PCR in 384-well plates in an extended study cohort of 91 primary melanomas. As described above, mRNA copy numbers were estimated from the cycle threshold (Ct) with similar assumptions made, except that a single mRNA copy yields a Ct of 40 (in TaqMan-based single-well PCR). Among these 11 candidate genes, the inventors identified a nine-gene signature that predicted the overall survival, independently of conventional staging methods, as evaluated by using Cox univariate and multivariate regression analyses. The prognostic significance of the nine-gene signature in predicting clinical outcome was successfully validated by real-time RT-PCR analysis in 384-well plates of an independent validation cohort of 45 primary melanomas.

Accordingly, a first aspect of the present invention relates to a method of predicting the clinical and/or treatment outcome in malignant melanoma, comprising determining the expression level of one or more prognostic RNA transcripts, or their corresponding cDNAs, or their expression products, in a sample comprising melanoma cells obtained from a patient, wherein said transcript(s) or expression products is/are the transcript or expression product of one or more genes selected from the group consisting of: KRT9, KBTBD10, and SPINK7/ECG2; wherein (a) for every unit of increased expression of KRT9, or the corresponding cDNA or expression product, said patient is expected to have a promising clinical outcome; and (b) for every unit of increased expression of KBTBD10, and/or SPINK7/ECG2, or the corresponding cDNAs or expression product(s), said patient is expected to have a poor clinical outcome.

The term "predicting clinical and/or treatment outcome" is used herein to refer to the prediction of the likelihood of cancer progression, including survival, recurrence, metastatic spread, and drug resistance, optionally following surgical removal of the primary tumor, chemotherapy, molecular therapy, immunotherapy and/or radiation therapy. The method of the invention may be used clinically in order to determine the best treatment modalities and regimen and/or to evaluate whether said patient is likely to respond favourably to a treatment, such as surgical intervention, chemotherapy, molecular therapy, immunotherapy and/or radiation therapy, in particular with regard to dosage and/or drug combinations.

A "clinical and/or therapeutic outcome" as used herein refers to a median overall survival of the patient as a consequence of cancer progression, recurrence, metastatic spread, and drug resistance. Hence, a patient may expect a poor or a promising clinical outcome. "Poor clinical outcome" as used herein means that the patient is expected to have a median overall survival of less than five years, preferably less than four years, more preferably less than three years. In contrast, "promising clinical outcome" means that the patient is likely to have a median overall survival which is longer than the median overall survival of a patient expected to have a poor clinical outcome. For example, a patient being expected having a "promising clinical outcome" is expected to have a median overall survival of more than five years, preferably more than seven years, more preferably more than ten years. Moreover, "promising clinical outcome" may be additionally accompanied by one or more of the following: inhibition or slowing down of tumor growth, reduction in the number of tumor cells, reduction in tumor size, inhibition or slowing down of tumor cell infiltration into adjacent peripheral tissues, inhibition of metastasis, enhancement of anti-tumor response, and (partial) relief of at least one symptom associated with the tumor.

The term "malignant melanoma" refers to a malignant tumor of melanocytes, which is predominantly found in skin but also in mucosal tissue (e.g., the bowel) and the eye. Malignant melanoma is one of the rarer types of skin cancer but causes 75% of skin cancer related deaths. "Malignant melanoma" as used herein includes lentigo maligna, lentigo maligna melanoma, superficially spreading melanoma, acral lentiginous melanoma, mucosal melanoma, nodular melanoma, polypoid melanoma, desmoplastic melanoma, amelanotic melanoma, and soft-tissue melanoma.

In order to determine the expression level of one or more prognostic RNA transcripts, or their corresponding cDNAs, or their expression products of one or more genes, a sample comprising melanoma cells and, thus, the prognostic RNA transcripts or their expression products is first derived from a malignant melanoma.

The term "sample", as used herein, refers to a sample comprising melanoma cells, which cells may be homogenized and disrupted in order to release and optionally isolate the prognostic RNA transcripts. Said RNA transcripts may subsequently be used directly or processed into another form, such as cRNA, cDNA or PCR amplification products, which still represent the expressed genes in said sample of melanoma cells, i.e. the transcripts of these genes. RNA can be isolated according to any of a number of methods well known to those of skill in the art. For example, mRNA is isolated using oligo d(T) column chromatography or glass beads. Alternatively, a cDNA may be reverse transcribed from said prognostic RNA transcript, RNA transcribed from that cDNA, a DNA amplified from that cDNA, RNA transcribed from the amplified DNA, or the like. Total mRNA can be converted to cDNA and amplified by conventional procedures, for example, by reverse transcription in a per se known manner. A cDNA may be amplified by any of a variety of conventional amplification procedures, including PCR. Suitable PCR primers can be selected using any well-known methods.

For example, the level of expression of a prognostic RNA transcript or their corresponding cDNA in a sample is determined by hybridizing said RNA transcript or corresponding cDNA to a detectable probe, e.g. by performing a microarray. Then, the mRNA copy number may be calculated from the amount of hybridization, which generally reflects the level of expression of the polynucleotide in the melanoma cells, normalized to the amount of total tumor RNA (or cDNA) or to the expression level of one or more housekeeping genes.

Methods for detecting hybridization are well known in the art. For example, the prognostic RNA transcript or corresponding cDNA may be labelled with a fluorescent label and levels and patterns of fluorescence indicative of hybridization are measured, e.g. by fluorescence microscopy, preferably confocal fluorescence microscopy. In this detection method, an argon ion laser excites the fluorescent label, emissions are directed to a photomultiplier and the amount of emitted light detected and quantitated. The detected signals are considered to be proportional to the amount of probe/target hybridization complex at each position of the microarray. Further, the fluorescence microscope may be associated with a computer-driven scanner device to generate a quantitative two-dimensional image of hybridization intensity. The scanned image is examined to determine the abundance/expression level of each hybridized target transcript. Alternatively, a fluorescent imaging device, such as a microarray scanner, may be used.

Typically, array fluorescence intensities can be normalized to take into account variations in hybridization intensities when more than one array is used under similar test conditions. This may be achieved by using the intensities derived from internal normalization controls contained on each microarray, e.g. from housekeeping genes. Accordingly, "normalized" refers to the expression level of an RNA transcript relative to the expression level of the total RNA or relative to the expression level of a housekeeping gene. Housekeeping genes are genes that are constitutively transcribed at a relatively constant level across many or all known conditions, since the housekeeping gene's products are typically needed for maintenance of the cell. Examples of housekeeping genes include actin, GAPDH, and ubiquitin.

However, further methods for determining the amount of a polynucleotide are well known in the art and may include any suitable quantitative method. Examples for such further methods are, for example, quantitative PCR, such as real-time PCR, or reverse transcription PCR (RT-PCR), using primers specific for those polynucleotides. Methods for selecting suitable primers for detecting and quantitating the amplified product are known in the art and exemplified in the Examples section below.

Alternatively, the expression level may be determined by the expression product(s), i.e. by the polypeptides encoded by said genes. This may be accomplished using immunological methods involving the use of antibodies directed against said polypeptides, e.g. the expression level of the corresponding expression product(s) is determined by ELISA or immunohistochemistry.

In order to perform an ELISA the sample with an unknown amount of expression product is immobilized on a solid support either non-specifically via adsorption to the surface of the solid support or specifically by a so called capture-antibody specific to the expression product. After the antigen is immobilized the detection antibody is added, forming a complex with the antigen. The detection antibody can itself be covalently linked to an enzyme, or can be detected by a secondary antibody linked to an enzyme. Between each step the plate is typically washed with a mild detergent solution to remove any proteins or antibodies that are not specifically bound. Detection occurs by adding an enzymatic substrate to produce a visible signal, which indicates the quantity of expression product in the sample. Immunohistochemistry (IHC) refers to a method involving localizing the expression product in said melanoma cells using fluorescence labelled antibodies and determining the fluorescence intensity.

However, any suitable method may be used for determining the expression level of said expression product(s), such as by way of flow cytometry or surface plasmon resonance.

Accordingly, in a preferred embodiment, the expression level is determined by DNA microarray analysis or real-time PCR and subsequent calculation of the mRNA copy number normalized to the amount of total tumor RNA or to the expression level of one or more housekeeping genes; or wherein the expression level of the corresponding expression product(s) is determined by ELISA or immunohistochemistry.

The term "every unit of increased expression" as used herein refers to an expression level of one or more prognostic RNA transcripts, or their corresponding cDNAs, or their expression product(s) that has been found differentially expressed in short-term vs. long-term survivors. Thus, the higher the expression level of a gene which is predominantly expressed in tumors of patients who had a short-term survival, the higher is the likelihood that the patient suffering from this tumor is a short-term survivor, i.e. is expected to have a poor clinical outcome. In contrast, the higher the expression level of a gene which is predominantly expressed in tumors of patients who are long-term survivors, the higher is the likelihood that the patient suffering from this tumor is a long-term survivor, i.e. is expected to have a promising clinical outcome.

The term "one or more" as used herein means that either one, or two, or all three expression level(s) of said genes is/are determined, i.e. either the expression level of KRT9, or KBTBD10, or SPINK7/ECG2, or KRT9 and KBTBD10, or KRT9 and SPINK7/ECG2, or KBTBD10 and SPINK7/ECG2, or KRT9 and KBTBD10 and SPINK7/ECG2.

In a preferred embodiment, the method comprises determining the expression level of two of said prognostic transcripts, or their corresponding cDNAs, or their expression products. In another preferred embodiment, the method comprises determining the expression level of all of said prognostic transcripts, or their corresponding cDNAs, or their expression products, i.e. of KRT9 and KBTBD10 and SPINK7/ECG2.

In still another preferred embodiment, the method of the invention further comprises determining the prognostic transcript of one or more genes selected from the group of genes consisting of: DCD, HES6, COL6A6, PIP, SCGB1D2, and SCGB2A2; or their corresponding cDNAs, or their expression products, wherein (a) for every unit of increased expression of HES6, or the corresponding cDNA or expression product, said patient is expected to have a poor clinical outcome; and (b) for every unit of increased expression of one or more of DCD, COL6A6, PIP, SCGB1D2, and SCGB2A2, or the corresponding cDNAs or expression product(s), said patient is expected to have a promising clinical outcome.

Consequently, the expression level of either KRT9 and DCD, or KRT9 and HES6, or KRT9 and COL6A6, or KRT9 and PIP, or KRT9 and SCGB1D2, or KRT9 and SCGB2A2, or KRT9 and DCD and HES6, or KRT9 and DCD and COL6A6, or KRT9 and DCD and PIP, or KRT9 and DCD and SCGB1D2, or KRT9 and DCD and SCGB2A2, or KRT9 and HES6 and COL6A6, or KRT9 and HES6 and PIP, or KRT9 and HES6 and SCGB1D2, or KRT9 and HES6 and SCGB2A2, or KRT9 and COL6A6 and PIP, or KRT9 and COL6A6 and SCGB1D2, or KRT9 and COL6A6 and SCGB2A2, or KRT9 and PIP and SCGB1D2, or KRT9 and PIP and SCGB2A2, or KRT9 and SCGB1D2 and SCGB2A2, or KRT9 and DCD and HES6 and COL6A6, or KRT9 and DCD and HES6 and PIP, or KRT9 and DCD and HES6 and SCGB1D2, or KRT9 and DCD and HES6 and SCGB2A2, or KRT9 and DCD and COL6A6 and PIP, or KRT9 and DCD and COL6A6 and SCGB1D2, or KRT9 and DCD and COL6A6 and SCGB2A2, or KRT9 and DCD and PIP and SCGB1D2, or KRT9 and DCD and PIP and SCGB2A2, or KRT9 and DCD and SCGB1D2 and SCGB2A2, or KRT9 and HES6 and COL6A6 and PIP, or KRT9 and HES6 and COL6A6 and SCGB1D2, or KRT9 and HES6 and COL6A6 and SCGB2A2, or KRT9 and HES6 and PIP and SCGB1D2, or KRT9 and HES6 and PIP and SCGB2A2, or KRT9 and HES6 and SCGB2A2 and SCGB1D2, or KRT9 and COL6A6 and PIP and SCGB1D2, or KRT9 and COL6A6 and PIP and SCGB2A2, or KRT9 and COL6A6 and SCGB1D2 and SCGB2A2, or KRT9 and PIP and SCGB1D2 and SCGB2A2, or KRT9 and DCD and HES6 and COL6A6 and PIP, or KRT9 and DCD and HES6 and COL6A6 and SCGB1D2, or KRT9 and DCD and HES6 and COL6A6 and SCGB2A2, or KRT9 and DCD and HES6 and PIP and SCGB1D2, or KRT9 and DCD and HES6 and PIP and SCGB2A2, or KRT9 and DCD and HES6 and SCGB1D2 and SCGB2A2, or KRT9 and HES6 and COL6A6 and PIP and SCGB1D2, or KRT9 and HES6 and COL6A6 and PIP and SCGB2A2, or KRT9 and HES6 and COL6A6 and SCGB1D2 and SCGB2A2, or KRT9 and HES6 and PIP and SCGB1D2 and SCGB2A2, or KRT9 and DCD and COL6A6 and PIP and SCGB1D2, or KRT9 and COL6A6 and PIP and SCGB1D2 and SCGB2A2, or KRT9 and PIP and SCGB1D2 and SCGB2A2 and DCD, or KRT9 and SCGB1D2 and SCGB2A2 and DCD and COL6A6, or KRT9 and SCGB2A2 and DCD and COL6A6 and PIP, or KRT9 and HES6 and COL6A6 and PIP and SCGB1D2 and SCGB2A2, or KRT9 and DCD and HES6 and PIP and SCGB1D2 and SCGB2A2, or KRT9 and DCD and HES6 and COL6A6 and SCGB1D2 and SCGB2A2, or KRT9 and DCD and HES6 and COL6A6 and PIP and SCGB2A2, or KRT9 and DCD and HES6 and COL6A6 and PIP and SCGB1D2, or KRT9 and DCD and COL6A6 and PIP and SCGB1D2 and SCGB2A2;

or KBTBD10 and DCD, or KBTBD10 and HES6, or KBTBD10 and COL6A6, or KBTBD10 and PIP, or KBTBD10 and SCGB1D2, or KBTBD10 and SCGB2A2, or KBTBD10 and DCD and HES6, or KBTBD10 and DCD and COL6A6, or KBTBD10 and DCD and PIP, or KBTBD10 and DCD and SCGB1D2, or KBTBD10 and DCD and SCGB2A2, or KBTBD10 and HES6 and COL6A6, or KBTBD10 and HES6 and PIP, or KBTBD10 and HES6 and SCGB1D2, or KBTBD10 and HES6 and SCGB2A2, or KBTBD10 and COL6A6 and PIP, or KBTBD10 and COL6A6 and SCGB1D2, or KBTBD10 and COL6A6 and SCGB2A2, or KBTBD10 and PIP and SCGB1D2, or KBTBD10 and PIP and SCGB2A2, or KBTBD10 and SCGB1D2 and SCGB2A2, or KBTBD10 and DCD and HES6 and COL6A6, or KBTBD10 and DCD and HES6 and PIP, or KBTBD10 and DCD and HES6 and SCGB1D2, or KBTBD10 and DCD and HES6 and SCGB2A2, or KBTBD10 and DCD and COL6A6 and PIP, or KBTBD10 and DCD and COL6A6 and SCGB1D2, or KBTBD10 and DCD and COL6A6 and SCGB2A2, or KBTBD10 and DCD and PIP and SCGB1D2, or KBTBD10 and DCD and PIP and SCGB2A2, or KBTBD10 and DCD and SCGB1D2 and SCGB2A2, or KBTBD10 and HES6 and COL6A6 and PIP, or KBTBD10 and HES6 and COL6A6 and SCGB1D2, or KBTBD10 and HES6 and COL6A6 and SCGB2A2, or KBTBD10 and HES6 and PIP and SCGB1D2, or KBTBD10 and HES6 and PIP and SCGB2A2, or KBTBD10 and HES6 and SCGB2A2 and SCGB1D2, or KBTBD10 and COL6A6 and PIP and SCGB1D2, or KBTBD10 and COL6A6 and PIP and SCGB2A2, or KBTBD10 and COL6A6 and SCGB1D2 and SCGB2A2, or KBTBD10 and PIP and SCGB1D2 and SCGB2A2, or KBTBD10 and DCD and HES6 and COL6A6 and PIP, or KBTBD10 and DCD and HES6 and COL6A6 and SCGB1D2, or KBTBD10 and DCD and HES6 and COL6A6 and SCGB2A2, or KBTBD10 and DCD and HES6 and PIP and SCGB1D2, or KBTBD10 and DCD and HES6 and PIP and SCGB2A2, or KBTBD10 and DCD and HES6 and SCGB1D2 and SCGB2A2, or KBTBD10 and DCD and COL6A6 and PIP and SCGB1D2, or KBTBD10 and DCD and COL6A6 and PIP and SCGB2A2, or KBTBD10 and DCD and COL6A6 and SCGB1D2 and SCGB2A2, or KBTBD10 and DCD and PIP and SCGB1D2 and SCGB2A2, or KBTBD10 and HES6 and COL6A6 and PIP and SCGB1D2, or KBTBD10 and HES6 and COL6A6 and PIP and SCGB2A2, or KBTBD10 and HES6 and COL6A6 and SCGB1D2 and SCGB2A2, or KBTBD10 and HES6 and PIP and SCGB1D2 and SCGB2A2, or KBTBD10 and DCD and COL6A6 and PIP and SCGB1D2, or KBTBD10 and COL6A6 and PIP and SCGB1D2 and SCGB2A2, or KBTBD10 and PIP and SCGB1D2 and SCGB2A2 and DCD, or KBTBD10 and SCGB1D2 and SCGB2A2 and DCD and COL6A6, or KBTBD10 and SCGB2A2 and DCD and COL6A6 and PIP, or KBTBD10 and HES6 and COL6A6 and PIP and SCGB1D2 and SCGB2A2, or KBTBD10 and DCD and HES6 and PIP and SCGB1D2 and SCGB2A2, or KBTBD10 and DCD and HES6 and COL6A6 and SCGB1D2 and SCGB2A2, or KBTBD10 and DCD and HES6 and COL6A6 and PIP and SCGB2A2, or KBTBD10 and DCD and HES6 and COL6A6 and PIP and SCGB1D2 and SCGB2A2;

or SPINK7/ECG2 and DCD, or SPINK7/ECG2 and HES6, or SPINK7/ECG2 and COL6A6, or SPINK7/ECG2 and PIP, or SPINK7/ECG2 and SCGB1D2, or SPINK7/ECG2 and SCGB2A2, or SPINK7/ECG2 and DCD and HES6, or SPINK7/ECG2 and DCD and COL6A6, or SPINK7/ECG2 and DCD and PIP, or SPINK7/ECG2 and DCD and SCGB1D2, or SPINK7/ECG2 and DCD and SCGB2A2, or SPINK7/ECG2 and HES6 and COL6A6, or SPINK7/ECG2 and HES6 and PIP, or SPINK7/ECG2 and HES6 and SCGB1D2, or SPINK7/ECG2 and HES6 and SCGB2A2, or SPINK7/ECG2 and COL6A6 and PIP, or SPINK7/ECG2 and COL6A6 and SCGB1D2, or SPINK7/ECG2 and COL6A6 and SCGB2A2, or SPINK7/ECG2 and PIP and SCGB1D2, or SPINK7/ECG2 and PIP and SCGB2A2, or SPINK7/ECG2 and SCGB1D2 and SCGB2A2, or SPINK7/ECG2 and DCD and HES6 and COL6A6, or SPINK7/ECG2 and DCD and HES6 and PIP, or SPINK7/ECG2 and DCD and HES6 and SCGB1D2, or SPINK7/ECG2 and DCD and HES6 and SCGB2A2, or SPINK7/ECG2 and DCD and COL6A6 and PIP, or SPINK7/ECG2 and DCD and COL6A6 and SCGB1D2, or SPINK7/ECG2 and DCD and COL6A6 and SCGB2A2, or SPINK7/ECG2 and DCD and PIP and SCGB1D2, or SPINK7/ECG2 and DCD and PIP and SCGB2A2, or SPINK7/ECG2 and DCD and SCGB1D2 and SCGB2A2, or SPINK7/ECG2 and HES6 and COL6A6 and PIP, or SPINK7/ECG2 and HES6 and COL6A6 and SCGB1D2, or SPINK7/ECG2 and HES6 and COL6A6 and SCGB2A2, or SPINK7/ECG2 and HES6 and PIP and SCGB1D2, or SPINK7/ECG2 and HES6 and PIP and SCGB2A2, or SPINK7/ECG2 and HES6 and SCGB2A2 and SCGB1D2, or SPINK7/ECG2 and COL6A6 and PIP and SCGB1D2, or SPINK7/ECG2 and COL6A6 and PIP and SCGB2A2, or SPINK7/ECG2 and COL6A6 and SCGB1D2 and SCGB2A2, or SPINK7/ECG2 and PIP and SCGB1D2 and SCGB2A2, or SPINK7/ECG2 and DCD and HES6 and COL6A6 and PIP, or SPINK7/ECG2 and DCD and HES6 and COL6A6 and SCGB1D2, or SPINK7/ECG2 and DCD and HES6 and COL6A6 and SCGB2A2, or SPINK7/ECG2 and DCD and HES6 and PIP and SCGB1D2, or SPINK7/ECG2 and DCD and HES6 and PIP and SCGB2A2, or SPINK7/ECG2 and DCD and HES6 and SCGB1D2 and SCGB2A2, or SPINK7/ECG2 and HES6 and COL6A6 and PIP and SCGB1D2, or SPINK7/ECG2 and HES6 and COL6A6 and PIP and SCGB2A2, or SPINK7/ECG2 and HES6 and COL6A6 and SCGB1D2 and SCGB2A2, or SPINK7/ECG2 and HES6 and PIP and SCGB1D2 and SCGB2A2, or SPINK7/ECG2 and DCD and COL6A6 and PIP and SCGB1D2, or SPINK7/ECG2 and COL6A6 and PIP and SCGB1D2 and SCGB2A2, or SPINK7/ECG2 and PIP and SCGB1D2 and SCGB2A2 and DCD, or SPINK7/ECG2 and SCGB1D2 and SCGB2A2 and DCD and COL6A6, or SPINK7/ECG2 and SCGB2A2 and DCD and COL6A6 and PIP, or SPINK7/ECG2 and HES6 and COL6A6 and PIP and SCGB1D2 and SCGB2A2, or SPINK7/ECG2 and DCD and HES6 and PIP and SCGB1D2 and SCGB2A2, or SPINK7/ECG2 and DCD and HES6 and COL6A6 and SCGB1D2 and SCGB2A2, or SPINK7/ECG2 and DCD and HES6 and COL6A6 and PIP and SCGB2A2, or SPINK7/ECG2 and DCD and HES6 and COL6A6 and PIP and SCGB1D2, or SPINK7/ECG2 and DCD and COL6A6 and PIP and SCGB1D2 and SCGB2A2;

or KRT9 and KBTBD10 and DCD, or KRT9 and KBTBD10 and HES6, or KRT9 and KBTBD10 and COL6A6, or KRT9 and KBTBD10 and PIP, or KRT9 and KBTBD10 and SCGB1D2, or KRT9 and KBTBD10 and SCGB2A2, or KRT9 and KBTBD10 and DCD and HES6, or KRT9 and KBTBD10 and DCD and COL6A6, or KRT9 and KBTBD10 and DCD and PIP, or KRT9 and KBTBD10 and DCD and SCGB1D2, or KRT9 and KBTBD10 and DCD and SCGB2A2, or KRT9 and KBTBD10 and HES6 and COL6A6, or KRT9 and KBTBD10 and HES6 and PIP, or KRT9 and KBTBD10 and HES6 and SCGB1D2, or KRT9 and KBTBD10 and HES6 and SCGB2A2, or KRT9 and KBTBD10 and COL6A6 and PIP, or KRT9 and KBTBD10 and COL6A6 and SCGB1D2, or KRT9 and KBTBD10 and COL6A6 and SCGB2A2, or KRT9 and KBTBD10 and PIP and SCGB1D2, or KRT9 and KBTBD10 and PIP and SCGB2A2, or KRT9 and KBTBD10 and SCGB1D2 and SCGB2A2, or KRT9 and KBTBD10 and DCD and HES6 and COL6A6, or KRT9 and KBTBD10 and DCD and HES6 and PIP, or KRT9 and KBTBD10 and DCD and HES6 and SCGB1D2, or KRT9 and KBTBD10 and DCD and HES6 and SCGB2A2, or KRT9 and KBTBD10 and DCD and COL6A6 and PIP, or KRT9 and KBTBD10 and DCD and COL6A6 and SCGB1D2, or KRT9 and KBTBD10 and DCD and COL6A6 and SCGB2A2, or KRT9 and KBTBD10 and DCD and PIP and SCGB1D2, or KRT9 and KBTBD10 and DCD and PIP and SCGB2A2, or KRT9 and KBTBD10 and DCD and SCGB1D2 and SCGB2A2, or KRT9 and KBTBD10 and HES6 and COL6A6 and PIP, or KRT9 and KBTBD10 and HES6 and COL6A6 and SCGB1D2, or KRT9 and KBTBD10 and HES6 and COL6A6 and SCGB2A2, or KRT9 and KBTBD10 and HES6 and PIP and SCGB1D2, or KRT9 and KBTBD10 and HES6 and PIP and SCGB2A2, or KRT9 and KBTBD10 and HES6 and SCGB2A2 and SCGB1D2, or KRT9 and KBTBD10 and COL6A6 and PIP and SCGB1D2, or KRT9 and KBTBD10 and COL6A6 and PIP and SCGB2A2, or KRT9 and KBTBD10 and COL6A6 and SCGB1D2 and SCGB2A2, or KRT9 and KBTBD10 and PIP and SCGB1D2 and SCGB2A2, or KRT9 and KBTBD10 and DCD and HES6 and COL6A6 and PIP, or KRT9 and KBTBD10 and DCD and HES6 and COL6A6 and SCGB1D2, or KRT9 and KBTBD10 and DCD and HES6 and COL6A6 and SCGB2A2, or KRT9 and KBTBD10 and DCD and HES6 and PIP and SCGB1D2, or KRT9 and KBTBD10 and DCD and HES6 and PIP and SCGB2A2, or KRT9 and KBTBD10 and DCD and HES6 and SCGB1D2 and SCGB2A2, or KRT9 and KBTBD10 and HES6 and COL6A6 and PIP and SCGB1D2, or KRT9 and KBTBD10 and HES6 and COL6A6 and PIP and SCGB2A2, or KRT9 and KBTBD10 and HES6 and COL6A6 and SCGB1D2 and SCGB2A2, or KRT9 and KBTBD10 and HES6 and PIP and SCGB1D2 and SCGB2A2, or KRT9 and KBTBD10 and DCD and COL6A6 and PIP and SCGB1D2, or KRT9 and KBTBD10 and COL6A6 and PIP and SCGB1D2 and SCGB2A2, or KRT9 and KBTBD10 and PIP and SCGB1D2 and SCGB2A2 and DCD, or KRT9 and KBTBD10 and SCGB1D2 and SCGB2A2 and DCD and COL6A6, or KRT9 and KBTBD10 and SCGB2A2 and DCD and COL6A6 and PIP, or KRT9 and KBTBD10 and HES6 and COL6A6 and PIP and SCGB1D2 and SCGB2A2, or KRT9 and KBTBD10 and DCD and HES6 and PIP and SCGB1D2 and SCGB2A2, or KRT9 and KBTBD10 and DCD and HES6 and COL6A6 and SCGB1D2 and SCGB2A2, or KRT9 and KBTBD10 and DCD and HES6 and COL6A6 and PIP and SCGB2A2, or KRT9 and KBTBD10 and DCD and HES6 and COL6A6 and PIP and SCGB1D2, or KRT9 and KBTBD10 and DCD and COL6A6 and PIP and SCGB1D2 and SCGB2A2;

or KRT9 and SPINK7/ECG2 and DCD, or KRT9 and SPINK7/ECG2 and HES6, or KRT9 and SPINK7/ECG2 and COL6A6, or KRT9 and SPINK7/ECG2 and PIP, or KRT9 and SPINK7/ECG2 and SCGB1D2, or KRT9 and SPINK7/ECG2 and SCGB2A2, or KRT9 and SPINK7/ECG2 and DCD and HES6, or KRT9 and SPINK7/ECG2 and DCD and COL6A6, or KRT9 and SPINK7/ECG2 and DCD and PIP, or KRT9 and SPINK7/ECG2 and DCD and SCGB1D2, or KRT9 and SPINK7/ECG2 and DCD and SCGB2A2, or KRT9 and SPINK7/ECG2 and HES6 and COL6A6, or KRT9 and SPINK7/ECG2 and HES6 and PIP, or KRT9 and SPINK7/ECG2 and HES6 and SCGB1D2, or KRT9 and SPINK7/ECG2 and HES6 and SCGB2A2, or KRT9 and SPINK7/ECG2 and COL6A6 and PIP, or KRT9 and SPINK7/ECG2 and COL6A6 and SCGB1D2, or KRT9 and SPINK7/ECG2 and COL6A6 and SCGB2A2, or KRT9 and SPINK7/ECG2 and PIP and SCGB1D2, or KRT9 and SPINK7/ECG2 and PIP and SCGB2A2, or KRT9 and SPINK7/ECG2 and SCGB1D2 and SCGB2A2, or KRT9 and SPINK7/ECG2 and DCD and HES6 and COL6A6, or KRT9 and SPINK7/ECG2 and DCD and HES6 and PIP, or KRT9 and SPINK7/ECG2 and DCD and HES6 and SCGB1D2, or KRT9 and SPINK7/ECG2 and DCD and HES6 and SCGB2A2, or KRT9 and SPINK7/ECG2 and DCD and COL6A6 and PIP, or KRT9 and SPINK7/ECG2 and DCD and COL6A6 and SCGB1D2, or KRT9 and SPINK7/ECG2 and DCD and COL6A6 and SCGB2A2, or KRT9 and SPINK7/ECG2 and DCD and PIP and SCGB1D2, or KRT9 and SPINK7/ECG2 and DCD and PIP and SCGB2A2, or KRT9 and SPINK7/ECG2 and DCD and SCGB1D2 and SCGB2A2, or KRT9 and SPINK7/ECG2 and HES6 and COL6A6 and PIP, or KRT9 and SPINK7/ECG2 and HES6 and COL6A6 and SCGB1D2, or KRT9 and SPINK7/ECG2 and HES6 and COL6A6 and SCGB2A2, or KRT9 and SPINK7/ECG2 and HES6 and PIP and SCGB1D2, or KRT9 and SPINK7/ECG2 and HES6 and PIP and SCGB2A2, or KRT9 and SPINK7/ECG2 and HES6 and SCGB2A2 and SCGB1D2, or KRT9 and SPINK7/ECG2 and COL6A6 and PIP and SCGB1D2, or KRT9 and SPINK7/ECG2 and COL6A6 and PIP and SCGB2A2, or KRT9 and SPINK7/ECG2 and COL6A6 and SCGB1D2 and SCGB2A2, or KRT9 and SPINK7/ECG2 and PIP and SCGB1D2 and SCGB2A2, or KRT9 and SPINK7/ECG2 and DCD and HES6 and COL6A6 and PIP, or KRT9 and SPINK7/ECG2 and DCD and HES6 and COL6A6 and SCGB1D2, or KRT9 and SPINK7/ECG2 and DCD and HES6 and COL6A6 and SCGB2A2, or KRT9 and SPINK7/ECG2 and DCD and HES6 and PIP and SCGB1D2, or KRT9 and SPINK7/ECG2 and DCD and HES6 and PIP and SCGB2A2, or KRT9 and SPINK7/ECG2 and DCD and HES6 and SCGB1D2 and SCGB2A2, or KRT9 and SPINK7/ECG2 and DCD and COL6A6 and PIP and SCGB1D2, or KRT9 and SPINK7/ECG2 and HES6 and COL6A6 and PIP and SCGB2A2, or KRT9 and SPINK7/ECG2 and HES6 and COL6A6 and PIP and SCGB1D2, or KRT9 and SPINK7/ECG2 and HES6 and COL6A6 and SCGB1D2 and SCGB2A2, or KRT9 and SPINK7/ECG2 and HES6 and PIP and SCGB1D2 and SCGB2A2, or KRT9 and SPINK7/ECG2 and DCD and COL6A6 and PIP and SCGB1D2, or KRT9 and SPINK7/ECG2 and COL6A6 and PIP and SCGB1D2 and SCGB2A2, or KRT9 and SPINK7/ECG2 and PIP and SCGB1D2 and SCGB2A2 and DCD, or KRT9 and SPINK7/ECG2 and SCGB1D2 and SCGB2A2 and DCD and COL6A6, or KRT9 and SPINK7/ECG2 and SCGB2A2 and DCD and COL6A6 and PIP, or KRT9 and SPINK7/ECG2 and HES6 and COL6A6 and PIP and SCGB1D2 and SCGB2A2, or KRT9 and SPINK7/ECG2 and DCD and HES6 and PIP and SCGB1D2 and SCGB2A2, or KRT9 and SPINK7/ECG2 and DCD and HES6 and COL6A6 and SCGB1D2 and SCGB2A2, or KRT9 and SPINK7/ECG2 and DCD and HES6 and COL6A6 and PIP and SCGB2A2, or KRT9 and SPINK7/ECG2 and DCD and HES6 and COL6A6 and PIP and SCGB1D2, or KRT9 and SPINK7/ECG2 and DCD and COL6A6 and PIP and SCGB1D2 and SCGB2A2;

or KBTBD10 and SPINK7/ECG2 and DCD, or KBTBD10 and SPINK7/ECG2 and HES6, or KBTBD10 and SPINK7/ECG2 and COL6A6, or KBTBD10 and SPINK7/ECG2 and PIP, or KBTBD10 and SPINK7/ECG2 and SCGB1D2, or KBTBD10 and SPINK7/ECG2 and SCGB2A2, or KBTBD10 and SPINK7/ECG2 and DCD and HES6, or KBTBD10 and SPINK7/ECG2 and DCD and COL6A6, or KBTBD10 and SPINK7/ECG2 and DCD and PIP, or KBTBD10 and SPINK7/ECG2 and DCD and SCGB1D2, or KBTBD10 and SPINK7/ECG2 and DCD and SCGB2A2, or KBTBD10 and SPINK7/ECG2 and HES6 and COL6A6, or KBTBD10 and SPINK7/ECG2 and HES6 and PIP, or KBTBD10 and SPINK7/ECG2 and HES6 and SCGB1D2, or KBTBD10 and SPINK7/ECG2 and HES6 and SCGB2A2, or KBTBD10 and SPINK7/ECG2 and COL6A6 and PIP, or KBTBD10 and SPINK7/ECG2 and COL6A6 and SCGB1D2, or KBTBD10 and SPINK7/ECG2 and COL6A6 and SCGB2A2, or KBTBD10 and SPINK7/ECG2 and PIP and SCGB1D2, or KBTBD10 and SPINK7/ECG2 and PIP and SCGB2A2, or KBTBD10 and SPINK7/ECG2 and SCGB1D2 and SCGB2A2, or KBTBD10 and SPINK7/ECG2 and DCD and HES6 and COL6A6, or KBTBD10 and SPINK7/ECG2 and DCD and HES6 and PIP, or KBTBD10 and SPINK7/ECG2 and DCD and HES6 and SCGB1D2, or KBTBD10 and SPINK7/ECG2 and DCD and HES6 and SCGB2A2, or KBTBD10 and SPINK7/ECG2 and DCD and COL6A6 and PIP, or KBTBD10 and SPINK7/ECG2 and DCD and COL6A6 and SCGB1D2, or KBTBD10 and SPINK7/ECG2 and DCD and COL6A6 and SCGB2A2, or KBTBD10 and SPINK7/ECG2 and DCD and PIP and SCGB1D2, or KBTBD10 and SPINK7/ECG2 and DCD and PIP and SCGB2A2, or KBTBD10 and SPINK7/ECG2 and DCD and SCGB1D2 and SCGB2A2, or KBTBD10 and SPINK7/ECG2 and HES6 and COL6A6 and PIP, or KBTBD10 and SPINK7/ECG2 and HES6 and COL6A6 and SCGB1D2, or KBTBD10 and SPINK7/ECG2 and HES6 and COL6A6 and SCGB2A2, or KBTBD10 and SPINK7/ECG2 and HES6 and PIP and SCGB1D2, or KBTBD10 and SPINK7/ECG2 and HES6 and PIP and SCGB2A2, or KBTBD10 and SPINK7/ECG2 and HES6 and SCGB2A2 and SCGB1D2, or KBTBD10 and SPINK7/ECG2 and COL6A6 and PIP and SCGB1D2, or KBTBD10 and SPINK7/ECG2 and COL6A6 and PIP and SCGB2A2, or KBTBD10 and SPINK7/ECG2 and COL6A6 and SCGB1D2 and SCGB2A2, or KBTBD10 and SPINK7/ECG2 and PIP and SCGB1D2 and SCGB2A2, or KBTBD10 and SPINK7/ECG2 and DCD and HES6 and COL6A6 and PIP, or KBTBD10 and SPINK7/ECG2 and DCD and HES6 and COL6A6 and SCGB1D2, or KBTBD10 and SPINK7/ECG2 and DCD and HES6 and COL6A6 and SCGB2A2, or KBTBD10 and SPINK7/ECG2 and DCD and HES6 and PIP and SCGB1D2, or KBTBD10 and SPINK7/ECG2 and DCD and HES6 and PIP and SCGB2A2, or KBTBD10 and SPINK7/ECG2 and DCD and HES6 and SCGB1D2 and SCGB2A2, or KBTBD10 and SPINK7/ECG2 and HES6 and COL6A6 and PIP and SCGB1D2, or KBTBD10 and SPINK7/ECG2 and HES6 and COL6A6 and PIP and SCGB2A2, or KBTBD10 and SPINK7/ECG2 and HES6 and COL6A6 and SCGB1D2 and SCGB2A2, or KBTBD10 and SPINK7/ECG2 and HES6 and PIP and SCGB1D2 and SCGB2A2, or KBTBD10 and SPINK7/ECG2 and DCD and COL6A6 and PIP and SCGB1D2, or KBTBD10 and SPINK7/ECG2 and COL6A6 and PIP and SCGB1D2 and SCGB2A2, or KBTBD10 and SPINK7/ECG2 and PIP and SCGB1D2 and SCGB2A2 and DCD, or KBTBD10 and SPINK7/ECG2 and SCGB1D2 and SCGB2A2 and DCD and COL6A6, or KBTBD10 and SPINK7/ECG2 and SCGB2A2 and DCD and COL6A6 and PIP, or KBTBD10 and SPINK7/ECG2 and HES6 and COL6A6 and PIP and SCGB1D2 and SCGB2A2, or KBTBD10 and SPINK7/ECG2 and DCD and HES6 and PIP and SCGB1D2 and SCGB2A2, or KBTBD10 and SPINK7/ECG2 and DCD and HES6 and COL6A6 and SCGB1D2 and SCGB2A2, or KBTBD10 and SPINK7/ECG2 and DCD and HES6 and COL6A6 and PIP and SCGB2A2, or KBTBD10 and SPINK7/ECG2 and DCD and HES6 and COL6A6 and PIP and SCGB1D2, or KBTBD10 and SPINK7/ECG2 and DCD and COL6A6 and PIP and SCGB1D2 and SCGB2A2;

or KRT9 and KBTBD10 and SPINK7/ECG2 and DCD, or KRT9 and KBTBD10 and SPINK7/ECG2 and HES6, or KRT9 and KBTBD10 and SPINK7/ECG2 and COL6A6, or KRT9 and KBTBD10 and SPINK7/ECG2 and PIP, or KRT9 and KBTBD10 and SPINK7/ECG2 and SCGB1D2, or KRT9 and KBTBD10 and SPINK7/ECG2 and SCGB2A2, or KRT9 and KBTBD10 and SPINK7/ECG2 and DCD and HES6, or KRT9 and KBTBD10 and SPINK7/ECG2 and DCD and COL6A6, or KRT9 and KBTBD10 and SPINK7/ECG2 and DCD and PIP, or KRT9 and KBTBD10 and SPINK7/ECG2 and DCD and SCGB1D2, or KRT9 and KBTBD10 and SPINK7/ECG2 and DCD and SCGB2A2, or KRT9 and KBTBD10 and SPINK7/ECG2 and HES6 and COL6A6, or KRT9 and KBTBD10 and SPINK7/ECG2 and HES6 and PIP, or KRT9 and KBTBD10 and SPINK7/ECG2 and HES6 and SCGB1D2, or KRT9 and KBTBD10 and SPINK7/ECG2 and HES6 and SCGB2A2, or KRT9 and KBTBD10 and SPINK7/ECG2 and COL6A6 and PIP, or KRT9 and KBTBD10 and SPINK7/ECG2 and COL6A6 and SCGB1D2, or KRT9 and KBTBD10 and SPINK7/ECG2 and COL6A6 and SCGB2A2, or KRT9 and KBTBD10 and SPINK7/ECG2 and PIP and SCGB1D2, or KRT9 and KBTBD10 and SPINK7/ECG2 and PIP and SCGB2A2, or KRT9 and KBTBD10 and SPINK7/ECG2 and SCGB1D2 and SCGB2A2, or KRT9 and KBTBD10 and SPINK7/ECG2 and DCD and HES6 and COL6A6, or KRT9 and KBTBD10 and SPINK7/ECG2 and DCD and HES6 and PIP, or KRT9 and KBTBD10 and SPINK7/ECG2 and DCD and HES6 and SCGB1D2, or KRT9 and KBTBD10 and SPINK7/ECG2 and DCD and HES6 and SCGB2A2, or KRT9 and KBTBD10 and SPINK7/ECG2 and DCD and COL6A6 and PIP, or KRT9 and KBTBD10 and SPINK7/ECG2 and DCD and COL6A6 and SCGB1D2, or KRT9 and KBTBD10 and SPINK7/ECG2 and DCD and COL6A6 and SCGB2A2, or KRT9 and KBTBD10 and SPINK7/ECG2 and DCD and PIP and SCGB1D2, or KRT9 and KBTBD10 and SPINK7/ECG2 and DCD and PIP and SCGB2A2, or KRT9 and KBTBD10 and SPINK7/ECG2 and DCD and SCGB1D2 and SCGB2A2, or KRT9 and KBTBD10 and SPINK7/ECG2 and HES6 and COL6A6 and PIP, or KRT9 and KBTBD10 and SPINK7/ECG2 and HES6 and COL6A6 and SCGB1D2, or KRT9 and KBTBD10 and SPINK7/ECG2 and HES6 and COL6A6 and SCGB2A2, or KRT9 and KBTBD10 and SPINK7/ECG2 and HES6 and PIP and SCGB1D2, or KRT9 and KBTBD10 and SPINK7/ECG2 and HES6 and PIP and SCGB2A2, or KRT9 and KBTBD10 and SPINK7/ECG2 and HES6 and SCGB2A2 and SCGB1D2, or KRT9 and KBTBD10 and SPINK7/ECG2 and COL6A6 and PIP and SCGB1D2, or KRT9 and KBTBD10 and SPINK7/ECG2 and COL6A6 and PIP and SCGB2A2, or KRT9 and KBTBD10 and SPINK7/ECG2 and COL6A6 and SCGB1D2 and SCGB2A2, or KRT9 and KBTBD10 and SPINK7/ECG2 and PIP and SCGB1D2 and SCGB2A2, or KRT9 and KBTBD10 and SPINK7/ECG2 and DCD and HES6 and COL6A6 and PIP, or KRT9 and KBTBD10 and SPINK7/ECG2 and DCD and HES6 and COL6A6 and SCGB1D2, or KRT9 and KBTBD10 and SPINK7/ECG2 and DCD and HES6 and COL6A6 and SCGB2A2, or KRT9 and KBTBD10 and SPINK7/ECG2 and DCD and HES6 and PIP and SCGB1D2, or KRT9 and KBTBD10 and SPINK7/ECG2 and DCD and HES6 and PIP and SCGB2A2, or KRT9 and KBTBD10 and SPINK7/ECG2 and DCD and HES6 and SCGB1D2 and SCGB2A2, or KRT9 and KBTBD10 and SPINK7/ECG2 and HES6 and COL6A6 and PIP and SCGB1D2, or KRT9 and KBTBD10 and SPINK7/ECG2 and HES6 and COL6A6 and PIP and SCGB2A2, or KRT9 and KBTBD10 and SPINK7/ECG2 and HES6 and COL6A6 and SCGB1D2 and SCGB2A2, or KRT9 and KBTBD10 and SPINK7/ECG2 and HES6 and PIP and SCGB1D2 and SCGB2A2, or KRT9 and KBTBD10 and SPINK7/ECG2 and DCD and COL6A6 and PIP and SCGB1D2, or KRT9 and KBTBD10 and SPINK7/ECG2 and COL6A6 and PIP and SCGB1D2 and SCGB2A2, or KRT9 and KBTBD10 and SPINK7/ECG2 and PIP and SCGB1D2 and SCGB2A2 and DCD, or KRT9 and KBTBD10 and SPINK7/ECG2 and SCGB1D2 and SCGB2A2 and DCD and COL6A6, or KRT9 and KBTBD10 and SPINK7/ECG2 and SCGB2A2 and DCD and COL6A6 and PIP, or KRT9 and KBTBD10 and SPINK7/ECG2 and HES6 and COL6A6 and PIP and SCGB1D2 and SCGB2A2, or KRT9 and KBTBD10 and SPINK7/ECG2 and DCD and HES6 and PIP and SCGB1D2 and SCGB2A2, or KRT9 and KBTBD10 and SPINK7/ECG2 and DCD and HES6 and COL6A6 and SCGB1D2 and SCGB2A2, or KRT9 and KBTBD10 and SPINK7/ECG2 and DCD and HES6 and COL6A6 and PIP and SCGB2A2, or KRT9 and KBTBD10 and SPINK7/ECG2 and DCD and HES6 and COL6A6 and PIP and SCGB1D2, or KRT9 and KBTBD10 and SPINK7/ECG2 and DCD and COL6A6 and PIP and SCGB1D2 and SCGB2A2 may be determined.

In still another preferred embodiment, the method comprises determining the expression level of all of said prognostic transcripts, their cDNAs, or their expression products, i.e. of KRT9 and KBTBD10 and SPINK7/ECG2 and DCD and COL6A6 and PIP and SCGB1D2 and SCGB2A2.

Alternatively, the expression levels as determined in the method of the invention may be used in order to calculate a prognostic score. Accordingly, in a second aspect, the invention provides a method of predicting the clinical and/or treatment outcome with a human patient suffering from malignant melanoma, comprising (a) determining the expression level of one or more prognostic RNA transcripts, or their corresponding cDNAs, or their expression products, in a sample comprising melanoma cells obtained from the patient, wherein said transcript(s), cDNAs, or expression products is/are the transcript, cDNA, or expression product of one or more genes selected from the group consisting of: KRT9, KBTBD10, and SPINK7/ECG2; and (b) using a device for calculating a prognostic score for said patient, comprising coded values of genes selected.

The device may be a computer program run on a computer, or a calculator.

Following gene expression profiling of the respective genes, a risk score is calculated as the sum of the coded expression values (0=low risk, 1=high risk) of each gene of the nine-gene signature, multiplied by the corresponding regression coefficients obtained from multivariate Cox regression analysis, as known in the art. The resulting prognostic score is assigned to quantiles, to reflect the ratio of long-term vs. short-term survivors in the present study population. The gene expression values of the genes of the nine-gene signature can also be used in other ways to calculate risk of relapse and/or tumor-related death.

With regard to SPINK7/ECG2, KBTBD10, and KRT9, the prognostic score may be calculated as follows:

Prognostic(three-gene)score=0.73×SPINK7/ECG2+ 0.72×KBTBD10+1.16×KRT9;

wherein said patient having a prognostic score of less than 1.2 (Cut-off) is in a percentile of patients who are likely to have a survival of more than five years, whereas said patient having a prognostic score of 1.2 or more is in a percentile of patients who are likely to have a survival of less than five years.

With regard to only two of the three genes, the prognostic score may be calculated as follows:

$$\text{Prognostic (two-gene) score} = 0.93 \times SPINK7/ECG2 +$$
$$1.23 \times KRT9, \text{Cut-off } 1.0; \text{or}$$
$$= 0.91 \times KBTBD10 + 1.16 \times KRT9,$$
$$\text{Cut-off } 1.0; \text{or}$$
$$= 0.73 \times SPINK7/ECG2 + 0.82 \times$$
$$KBTBD10, \text{Cut-off } 0.8.$$

With regard to all nine genes, the prognostic score may be calculated as follows:

Prognostic(nine-gene)score=0.84×DCD+0.62× SPINK7/ECG2+0.37×HES6+0.64×KBTBD10+ 0.42×COL6A6−0.06×PIP−0.71×SCGB1D2+ 0.35×SCGB2A2+1.02×KRT9;

wherein said patient having a prognostic score of less than 1.46 (Cut-off) is in a percentile of patients who are likely to have a survival of more than five years, whereas said patient having a prognostic score of 1.46 or more is in a percentile of patients who are likely to have a survival of less than five years.

Depending on the experimental conditions, the algorithm may change including the regression coefficients and the cut-offs for the gene expression values and the risk score. Gene expression values and/or risk score may also be used as continuous variables. However, a person skilled in the art and in knowledge of the prognostic genes of the methods of the invention will know how to determine the algorithm and how to calculate the prognostic score.

The prediction obtained by the method according to the aforementioned aspects may be used to prepare a personalized genomics profile for a malignant melanoma which may be used to improve or control the malignant melanoma of a patient. Thus, in a third aspect, the invention provides a method of preparing a personalized genomics profile for a malignant melanoma of a patient, comprising the steps of: (a) determining the expression level of one or more prognostic RNA transcripts, or their corresponding cDNAs, or their expression products, in a sample comprising melanoma cells obtained from the patient, wherein the prognostic transcript or its cDNA or its expression product is the transcript or the cDNA or the expression product of one or more genes selected from the group consisting of: KRT9, KBTBD10, and SPINK7/ECG2, wherein the expression level is normalized against a reference gene; and (b) optionally comparing the expression level determined in step (a) to a baseline level, or calculating a prognostic score using a method according to the second aspect; and (c) creating a personalized genomics profile from the data obtained.

In a preferred embodiment said personalized profile includes recommendation for a treatment modality of said patient and/or prediction of treatment outcome.

The reference gene may be a housekeeping gene, as described above.

Further, the expression level may be optionally compared to a baseline level. As used herein, the term "baseline level" refers to the level of gene expression in normal melanocytes, e.g. in a sample from the patient or from a "pool" of samples derived from normal subjects; or from a pool of different tissues from normal subjects. Alternatively, the baseline level may be the expression level in malignant melanoma that is known to be a malignant melanoma of a long-term survivor, or of a short-term survivor, e.g., the average value from a pool or compilation of such malignant melanoma samples. Any of the above types of baseline values may be available in a database compiled from such values.

The preferred embodiments of the first aspect are also preferred embodiments of the second and third aspect.

Thus, for example, in a preferred embodiment of the method of the second and third aspect, the method comprises determining the expression level of two of the prognostic transcripts, or their corresponding cDNAs, or their expression products of KRT9, KBTBD10, and SPINK7/ECG2, as described above in detail.

And consequently, in one preferred embodiment, the method of the first and second aspect further comprises determining the expression level of one or more prognostic RNA transcripts, cDNAs, or expression products of one or more genes selected from the group consisting of DCD, HES6, COL6A6, PIP, SCGB1D2, and SCGB2A2, as described above in detail.

Furthermore, in another preferred embodiment, the method of the first and second aspect comprises determining the expression level of all of said prognostic transcripts, their cDNAs, or their expression products, as described above in detail.

Further, for a particular type of malignant melanoma, namely plantar (sole of foot) or palmar (hand inner side) melanoma, it was found that a specific combination of prognostic genes is useful. Accordingly, in one particular embodiment, in the methods of the invention the expression level of the prognostic transcripts or their expression products of KBTBD10 and/or SPINK7/ECG2, and optionally of one or more genes selected from the group consisting of DCD, HES6, COL6A6, PIP, SCGB1D2, and SCGB2A2 in said sample is determined; and wherein said melanoma cells are obtained from a plantar or palmar melanoma. Moreover, in a preferred embodiment of the methods of the invention, the patient is a mammal such as a dog, cat, pig, cow, sheep, horse, rodent, e.g. rat, mouse, and guinea pig, or a primate, e.g. gorilla, chimpanzee, and human, preferably the patient is a human.

In the following, the present invention is illustrated by figures and examples which are not intended to limit the scope of the present invention.

FIGURES

EXAMPLES

Patients and Tissue Specimens

Figure 1:
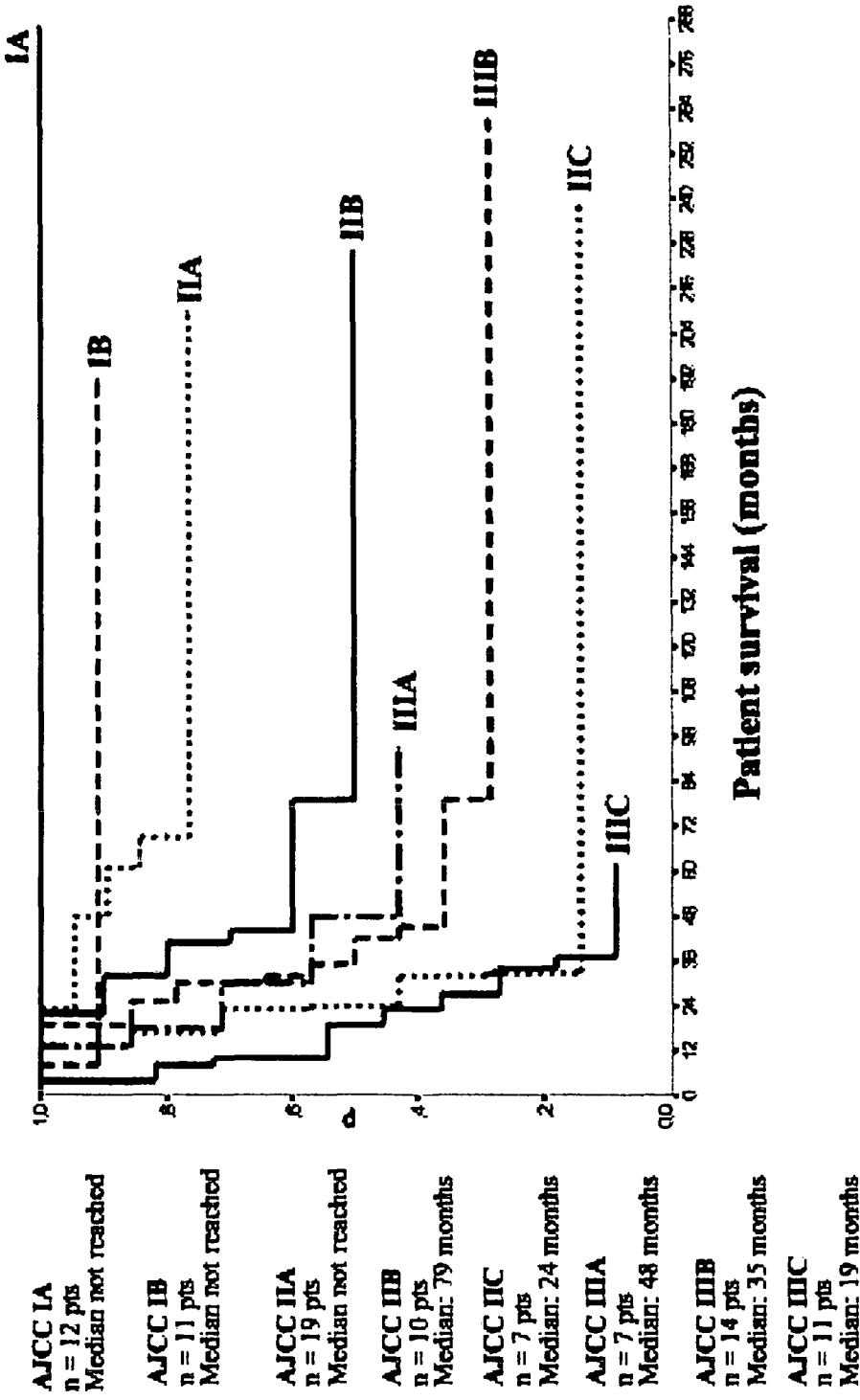
FIG. 1 shows Kaplan-Meier estimates of survival of the patient cohort. Overall survival is shown for the entire patient cohort of 91 patients with malignant melanoma, according to AJCC 2002 stages.

Following informed consent of the patients, fresh frozen tissue samples from primary cutaneous melanomas in the vertical growth phase were recruited for this study between 1983 and 2006 at the Fachklinik Hornheide in Münster, Germany (n=132; training, study, and validation set) and at the Ludwig-Maximilians-University of Munich, Germany (n=4: validation set). All patients were treated uniformly following standard regimens. Representative tissue specimens of the tumor (Breslow thickness 0.22-42 mm; containing 10-100% tumor tissue, as determined by hematoxylin-eosin staining of cryosections and review by a histopathologist) had been frozen in liquid nitrogen at the time of diagnosis and stored at −80° C. until use. Histological review of the cases was done on paraffin-embedded tissue. Tissue collection was approved by the local medical ethical committee of the Westfälische-Wilhelms-University of Munster. Clinical and follow-up data were retrieved from the melanoma data base of the Fachklinik Hornheide. The minimum clinical follow-up period was five years. The clinical and histopathological characteristics of the primary melanomas are summarized in Table 1. The overall survival probabilities of the study cohort of 91 patients according to AJCC 2002 stages are shown in FIG. 1.

TABLE 1

Clinical characteristics of the training, study, and validation cohorts.

| Characteristic | Training Cohort | Study Cohort* | Validation Cohort |
|---|---|---|---|
| No. of patients | 38 | 91 | 45 |
| Median age - yr (range) | 54 (19-88) | 57 (19-88) | 63 (37-81) |
| Sex - no. (%) | | | |
| Male | 17 (45) | 37 (41) | 17 (38) |
| Female | 21 (55) | 54 (59) | 28 (62) |
| Melanoma type | | | |
| SSM | 11 | 33 | 30 |
| ALM | 6 | 10 | 2 |
| NM | 4 | 9 | 4 |
| LMM | 3 | 4 | 2 |
| unclassified | 14 | 35 | 7 |
| Breslow thickness | | | |
| Median - mm (range) | 3.7 (1.0-35) | 2.9 (0.4-42) | 0.7 (0.2-10) |
| ≤1 mm - no. (%) | 2 (5) | 13 (14) | 29 (64) |

TABLE 1-continued

Clinical characteristics of the training, study, and validation cohorts.

| Characteristic | Training Cohort | Study Cohort* | Validation Cohort |
|---|---|---|---|
| 1.01-2 mm | 5 (13) | 19 (21) | 6 (13) |
| 2.01-4 mm | 15 (40) | 28 (31) | 5 (11) |
| >4 mm | 16 (42) | 31 (34) | 5 (11) |
| Clark level - no. (%) | | | |
| II | 0 (0) | 2 (2) | 8 (18) |
| III | 3 (8) | 10 (11) | 13 (29) |
| IV | 25 (66) | 60 (66) | 13 (29) |
| V | 10 (26) | 18 (20) | 2 (4) |
| unknown | 0 (0) | 1 (1) | 9 (20) |
| Ulceration - no. (%) | | | |
| Absent | 23 (61) | 59 (65) | 38 (84) |
| Present | 15 (39) | 32 (35) | 7 (16) |
| AJCC stage - at diagnosis | | | |
| IA | 2 (5) | 12 (13) | 24 (53) |
| IB | 2 (5) | 11 (12) | 7 (16) |
| IIA | 6 (16) | 19 (21) | 1 (2) |
| IIB | 7 (18) | 10 (11) | 4 (9) |
| IIC | 3 (8) | 7 (8) | 2 (4) |
| IIIA | 6 (16) | 7 (8) | 2 (4) |
| IIIB | 9 (24) | 14 (15) | 1 (2) |
| IIIC | 3 (8) | 11 (12) | — |
| Median follow-up - mo (range) | 48 (4-238) | 90 (4-286) | 81 (18-253) |

*The study population comprised the training population

The study cohort comprised 91 patients of the Fachklinik Hornheide with fresh frozen tissue available in 2005, when the study was initiated. From this study population, the inventors selected a training cohort of 38 patients representing the extreme ends of the entire range of patient survival (two groups of 19 patients each with the shortest and longest survival times, respectively). The validation cohort consisted of an independent group of 41 patients of the Fachklinik Hornheide (fresh frozen tissue and updates of follow-up available in 2009, when the study was concluded) and 4 patients from the Department of Dermatology and Allergology, Ludwig-Maximilians-University of Munich, Germany.

RNA Preparation and Reverse Transcription

Total RNA was extracted from cryosections of frozen primary melanoma samples by mechanical homogenization and purified using RNeasy Fibrous Tissue Mini Kits (Qiagen). RNA was quantified spectrophotometrically and RNA quality and integrity verified by agarose gel electrophoresis and staining with SYBR Green II (Fluka). Total RNA aliquots were reverse transcribed using MuLV Reverse Transcriptase (Applied Biosystems). Quality of the RT was verified by amplifying the house-keeping gene, 18S ribosomal RNA, using real-time PCR. Details of the RNA preparation and reverse transcription are described in Brunner et al.; Cancer Biother. Radiopharm., 2008.

RT-PCR Analysis

Expression of 92 genes, which were found to be differentially expressed (>3.5-fold) in primary melanomas of short-term vs. long-term survivors in our previous whole-genome DNA microarray analysis (Brunner et al.; Cancer Biother. Radiopharm., 2008), was quantified in the training population of 38 patients using real-time PCR on TaqMan Arrays (Applied Biosystems). Expression of 18S ribosomal RNA was analyzed in order to monitor RNA and cDNA quality. Duplicate 100-μl aliquots of cDNA of each tissue sample (normalized to 30 ng of tumor cDNA) were applied onto 384-well microfluidic cards, which were run on a 7900 HT Fast Real-Time PCR System (Applied Biosystems) at the Integrated Functional Genomics Center (IFG, University of Munster, Germany). mRNA copy numbers were estimated from the cycle threshold (Ct) with the assumptions made that, ideally, efficiency of reverse transcription and real-time PCR were uniform among different samples and that a single mRNA copy yields a Ct of 36 (on TaqMan Arrays). mRNA copy numbers were normalized to μg of total tumor RNA.

Expression of 11 candidate genes was quantified in the study population of 91 patients, using TaqMan real PCR (Applied Biosystems) in 384-well plates. Duplicate 10-μl aliquots of cDNA of each tissue sample (10 ng of total cDNA) were applied onto 384-well plates. As described above, mRNA copy numbers were estimated from the cycle threshold (Ct) with similar assumptions made, except that a single mRNA copy yields a Ct of 40 (in TaqMan-based single-well PCR).

Similarly, expression of the genes that are part of the 9-gene signature was quantified in the validation cohort of 45 patients.

Statistical Analysis

Following gene expression profiling of our previously identified set of 92 genes in the training population of 38 patients (19 short-term survivors [50%; 4-48 months] and 19 long-term survivors [50%; 61-238 months]), univariate Cox regression analysis was used to identify genes that, when dichotomized at the best univariate p value, were most powerful in discriminating between long and short overall survival. This analysis yielded 11 candidate genes.

Following gene expression profiling of these 11 candidate genes in the study population of 91 patients (36 short-term survivors [40%; 4-48 months] and 55 long-term survivors [60%; 61-286 months]), expression profiles for each gene were dichotomized into risk-related 40%- and 60%-quantiles, respectively, reflecting the ratio of short-term vs. long-term survivors in the study population. A risk score, based on a weighted nine-gene signature, was calculated as the sum of the coded values (0=low risk, 1=high risk) of each gene, multiplied by the corresponding regression coefficients obtained from multivariate Cox regression analysis. The resulting index (nine-gene score) was risk-dependently dichotomized into the corresponding quantiles (40 and 60%), again to reflect the ratio of long-term vs. short-term survivors in the population.

Selection of 11 Candidate Genes Predicting Clinical Outcome

Using whole-genome DNA microarray analysis, the inventors identified a set of 92 genes differentially expressed (>3.5-fold) in primary melanomas of short-term vs. long-term survivors, using an experimental strategy published previously (Brunner et al.; Cancer Biother. Radiopharm., 2008). In order to identify genes associated with overall survival, the inventors performed quantitative gene expression profiling of this set of genes in primary melanomas of the training cohort of 38 patients using real-time PCR on TaqMan Arrays.

Expression data for each gene were dichotomized at the best univariate p value. This expression analysis yielded 11 genes discriminating best between long and short survival: eight were protective genes (median overall survival ≤42 months vs. not reached) and three were risk genes (median overall survival not reached vs. ≤44 months) (Table 2). The median duration of follow-up in the training cohort was 48 months. All 11 genes were widely expressed in primary melanomas and were detected in 74-100% of the training cohort and in 87-100% of the study cohort of primary melanomas.

TABLE 2

Selection of Eleven Candidate Genes Based on the Correlation of Gene Expression Level and Patient Overall Survival (Training Cohort Comprising 38 Patients).

| Gene (prognosis) | UniGene Number | Detection* | Dichotomization# | Overall Survival ◊ | P value¶ |
|---|---|---|---|---|---|
| GBP4 (protective)‡ | Hs.409925 | 100 | 195.000 | 30-nr | 0.001 |
| DCD (protective) | Hs.350570 | 90 | 60.000 | 30-nr | 0.006 |
| SCGB2A2 (protective) | Hs.46452 | 87 | 97.000 | 32-nr | 0.006 |
| SPINK7/ECG2 (risk) | Hs.244569 | 90 | 8.300 | nr-32 | 0.009 |
| PIP (protective) | Hs.99949 | 84 | 105.000 | 32-nr | 0.011 |
| SCGB1D2 (protective) | Hs.204096 | 90 | 60.000 | 42-nr | 0.015 |
| COL6A6 (protective) | Hs.591282 | 100 | 22.000 | 30-nr | 0.016 |
| KRT9 (protective) | Hs.654569 | 97 | 80.000 | 32-nr | 0.021 |
| HES6 (risk) | Hs.42949 | 100 | 103.000 | nr-30 | 0.026 |
| MUC7 (protective) | Hs.631946 | 87 | 13.000 | 32-nr | 0.032 |
| KBTBD10 (risk) | Hs.50550 | 74 | 3.100 | nr-44 | 0.037 |

*Percentage of tumors expressing the respective gene.
Threshold value (estimated mRNA copy number/μg total RNA).
◊ Median overall survival (months) of patient cohorts dichotomized based on gene expression; nr—not reached.
¶P values for the association with overall survival were determined in univariate Cox regression analysis.
‡Protective genes were down-regulated during tumor progression and risk genes up-regulated.

A Nine-Gene Signature Associated with Overall Survival

Gene expression of these 11 candidate genes was analyzed in primary melanomas of the study cohort of 91 patients using real-time PCR on 384-well plates. Table 2 of the Supplementary Appendix lists the expression data for the 11 candidate genes in the 91 melanoma samples analyzed.

Expression data for each gene were dichotomized at risk-dependent quantiles reflecting the ratio of long-term vs. short-term survivors in the population. Expression profiles of the 11 genes in the study cohort were similar to those in the training cohort (Table 3). Dichotomization of the protective genes resulted in a median overall survival of ≤45 months vs. not reached, and dichotomization of the risk genes in a median overall survival of not reached vs. ≤48 months.

TABLE 3

Identification of the Nine-Gene Signature Based on the Correlation of Gene Expression Level and Patient Overall Survival (Study Cohort Comprising 91 Patients).

| Gene (prognosis) | UniGene Number | Dichotomization# | Overall Survival | P value¶ |
|---|---|---|---|---|
| KRT9 (protective)‡ | Hs.654569 | 11.904 | 35-nr ◊ | 0.001 |
| KBTBD10 (risk) | Hs.50550 | 6.322 | nr-45 | 0.003 |
| DCD (protective) | Hs.350570 | 889.862 | 41-nr | 0.004 |
| SPINK7/ECG2 (risk) | Hs.244569 | 16.185 | nr-45 | 0.006 |
| PIP (protective) | Hs.99949 | 43.081 | 41-nr | 0.007 |
| SCGB1D2 (protective) | Hs.204096 | 28.934 | 42-nr | 0.024 |
| SCGB2A2 (protective) | Hs.46452 | 58.943 | 42-nr | 0.025 |
| COL6A6 (protective) | Hs.591282 | 157.167 | 45-nr | 0.057 |
| HES6 (risk) | Hs.42949 | 62.789 | nr-48 | 0.096 |
| GBP4 (protective) | Hs.409925 | 467.166 | 45-nr | 0.144 |
| MUC-7 (protective) | Hs.631946 | 19.932 | nr-nr | 0.452 |

*Percentage of tumors expressing the respective gene.
Threshold value (estimated mRNA copy number/μg total RNA).
¶P values for the association with overall survival were determined in univariate Cox regression analysis.
◊ Median overall survival (months) of patient cohorts dichotomized based on gene expression; nr—not reached.
‡Protective genes were down-regulated during tumor progression and risk genes up-regulated.

Univariate Cox regression analysis indicated a significant association of protective as well as risk genes with overall survival (Table 3). Using a cut-off at a P value of 0.1, six protective (KRT9, DCD, PIP, SCGB1D2, SCGB2A2, COL6A6) and three risk genes (KBTBD10, SPINK7/ECG2, HES6) were selected to define a nine-gene signature. Based on this gene signature, a risk score was calculated as the sum of the coded expression data (low-risk=0, high-risk=1) weighted with the corresponding regression coefficient (R.C.) obtained from multivariate Cox regression analysis:

$$\text{Nine-gene score} = 0.84 \times DCD + 0.62 \times SPINK7/ECG2 + 0.37 \times HES6 + 0.64 \times KBTBD10 + 0.42 \times COL6A6 - 0.06 \times PIP - 0.71 \times SCGB1D2 + 0.35 \times SCGB2A2 + 1.02 \times KRT9$$

Following risk-dependent dichotomization of the study population at 5-yr survival-associated percentiles (40 and 60%) to reflect the ratio of long-term vs. short-term survivors in the population, a threshold risk score was identified. It is possible to use the expression of the above nine genes in other ways to calculate patient risk.

Figure 2A:
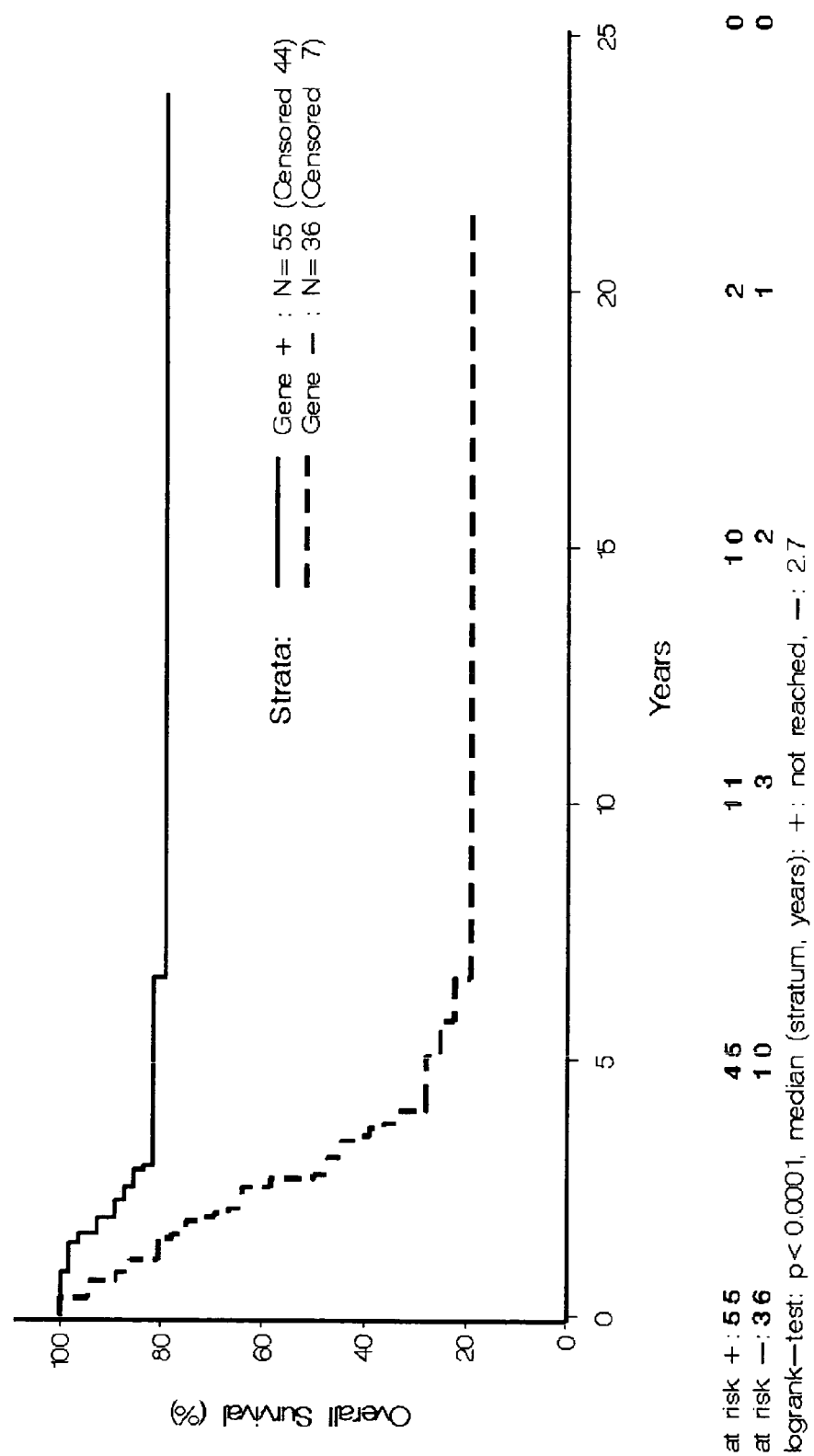
FIG. 2 shows Kaplan-Meier estimates of survival of patients with malignant melanoma according to the nine-gene signature and AJCC 2002 Staging. Overall survival is shown for the 91 patients of the study cohort with malignant melanoma, according to the nine-gene signature (FIG. 2A) and the combination of the nine-gene signature and AJCC staging (FIG. 2B).

By applying the above nine-gene score method to the study cohort (91 patients), a threshold risk score of 1.46 was identified (<1.46, low risk; ≥1.46, high risk). This risk score dichotomized the study population into 36 patients with high-risk gene signatures and 55 with low-risk gene signatures (Table 4). The nine-gene score was strongly associated with overall survival (p=0.0004). The misclassification rate was 22%. The median follow-up of the 91 patients was 90 months. The patients with a high-risk gene signature had a significantly shorter median overall survival than the patients with a low-risk gene signature (32 months [5-yr survival of 28%] vs. not reached [5-yr survival of 82%]; P<0.0001 by the log-rank test (FIG. 2A).

TABLE 4

Hazard Ratios for Overall Survival According to Multivariate Cox Regression Analysis based on the study cohort of 91 patients.

| Variable Study cohort | Range | Dichotomization | Hazard Ratio (95% CI) | P Value |
|---|---|---|---|---|
| Nine-gene score | 0-3.85 | 1.46# | 3.83 (1.82-8.04) | 0.0004 |
| Clinical score | IA-IIIC | I, IIA, IIB, IIIA-IIC, IIIB, IIIC | 3.90 (1.89-8.08) | 0.0002 |

Threshold value.

According to Cox multivariate regression analysis, comprising the nine-gene score and dichotomized clinical (age, sex) and histological parameters (AJCC 2002 staging, Breslow tumor thickness, lymph node status, ulceration), only the nine-gene score (hazard ratio=3.83, P<0.0004) and the AJCC stage (hazard ratio=3.90, P<0.0002) were significantly associated with overall survival (Table 4). Combination of both nine-gene score and AJCC stage significantly improved predictability of overall survival (FIG. 2B, P<0.0001), allowing for the designation of patients at extremely high risk (median overall survival of 30 months [5-yr survival probability of 15.0%]) vs. patients at extremely low risk (median overall survival not reached [5-yr survival probability of 95.4%]). The data demonstrate the special value of the genetic risk score in that it contains information which is not comprised in the conventional histopathological and clinical staging.

In order to validate the nine-gene signature, gene expression of the signature was analyzed in primary melanomas of a validation cohort of 45 patients (AJCC stages IA, IB, IIA, IIB, IIC, IIIA, IIIB) using real-time PCR on 384-well plates. Expression data for each gene were used to calculate the nine-gene risk score for each patient. The validation experiments confirmed that the nine-gene signature was strongly associated with overall survival. The misclassification rate was 31%.

Discussion

In this study, the inventors statistically correlated gene expression profiling and long-term survival data from patients with primary cutaneous malignant melanoma. A gene expression signature of primary tumors was identified which was associated with overall survival. Multivariate analyses showed that this signature was independent of conventional histopathological and clinical features.

When combining gene signature and conventional prognostic classifications, patients could be assigned to highly distinct risk groups, all of which comprised a broad spectrum of AJCC stages (as defined by tumor thickness, ulceration, and metastatic state upon first diagnosis). Notably, across AJCC stages I/IIA/IIB/IIIA, the genetic score allowed to identify patients with a 5-year survival probability of 95.4%. On the contrary, within the group of AJCC stage IIC/IIIB/IIIC patients, the gene expression signature of the present invention indicated a poor-prognosis subgroup with a 5-year survival probability of 15%, only.

These results have important implications for the future development of melanoma management. Currently, following first diagnosis and tumor resection, stage IB/II/III patients often receive year-long α-interferon-based protocols, irrespectively of their individual prognosis. Hence, within this group, a proportion of good-prognosis patients receive long term complex and often toxic treatment in the absence of proven therapeutic need or benefit. Further studies will, therefore, redefine the therapeutic impact of standard treatment regimens in various melanoma patient subgroups, characterized by prognostic gene expression patterns. For example, patients at lowest risk may eventually circumvent long-term medication and its toxicity. On the other hand, patients at highest risk may seek additional new treatment options beyond today's standard care.

REFERENCES

1. WO 2008/031041
2. Alonso S R, Tracey L. Ortiz P, et al. A high-throughput study in melanoma identifies epithelial-mesenchymal transition as a major determinant of metastasis. Cancer Res 2007; 67:3450-3460.
3. Bittner M, Meltzer P, Chen Y, et al. Molecular classification of cutaneous malignant melanoma by gene expression profiling. Nature 2000; 406:536-40.
4. Brunner G, Reitz M, Schwipper V, et al. Increased expression of the tumor suppressor PLZF is a continuous predictor of long-term survival in malignant melanoma patients. Cancer Biother Radiopharm 2008; 23:451-459.
5. Jaeger J, Koczan D, Thiesen H-J, et al. Gene expression signatures for tumor progression, tumor subtype, and tumor thickness in laser-microdissected melanoma tissues. Clin Cancer Res 2007; 13:806-15.
6. Katoh M and Katoh M. Integrative genomic analyses on HES/HEY family: Notch-independent HES1, HES3 transcription in undifferentiated ES cells, and Notch-dependent HES1, HES5, HEY1, HEY2, HEYL transcription in fetal tissues, adult tissues or cancer. Int. J. Oncol. 2007; 31: 461-466.
7. Ren S, Liu S, Howell P, et al. The Impact of Genomics in Understanding Human Melanoma Progression and Metastasis; Cancer Control 2008; 15(3): 202-215.
8. Riker A I, Enkemann S A, Fodstad O, et al. The gene expression profiles of primary and metastatic melanoma yields a transition point of tumor progression and metastasis. BMC Med Genomics 2008; 1:13.
9. Smith A P, Hoek K and Becker D. Whole-Genome Expression Profiling of the Melanoma Progression Pathway Reveals Marked Molecular Differences between Nevi/Melanoma In Situ and Advanced-Stage Melanomas. Cancer Biol & Ther 2005; 4(9): 1018-1029.
10. Winnepenninckx V, Lazar V, Michiels S, et al. Gene expression profiling of primary cutaneous melanoma and clinical outcome. J Natl Cancer Inst 2006; 98: 472-482.

The invention claimed is:

1. A method of predicting the clinical and/or treatment outcome in malignant melanoma, comprising:
   (a) processing into cDNA one or more prognostic RNA transcripts selected from the group consisting of KRT9, KBTBD1O, and SPINK7/ECG2, wherein the one or more prognostic RNA transcripts are obtained from a sample comprising melanoma cells obtained from a patient;
   (b) determining the expression level of the one or more prognostic RNA transcripts in said sample based on the cDNA processed in step (a), wherein
      (i) for every unit of increase of KRT9 cDNA processed in (a), said patient is expected to have a promising clinical outcome;
      (ii) for every unit of increase of KBTBD 10 cDNA and/or SPINK7/ECG2 cDNA processed in (a), said patient is expected to have a poor clinical outcome; and
   (c) providing to the patient a recommendation for standard treatment if there is an increase in a unit of KRT9 cDNA processed in (a), or providing to the patient a recommendation for aggressive treatment if there is an increase in a unit of KBTBD 10 cDNA and/or -SPINK7/ECG2 cDNA processed in (a).

2. A method of preparing a personalized genomics profile for a malignant melanoma of a patient, comprising the steps of:
   (a) processing into cDNA one or more prognostic RNA transcripts selected from the group consisting of KRT9, KBTBD1O, and SPINK7/ECG2, wherein the one or more prognostic RNA transcripts are obtained from a sample comprising melanoma cells obtained from a patient;
   (b) determining the expression level of one or more prognostic RNA transcripts in said sample based on their corresponding cDNA processed in step (a), wherein the expression level is normalized against a reference gene and the expression level is compared to a baseline level, and wherein
(i) for every unit of increase of KRT9 cDNA processed in step (a), said patient is expected to have a promising clinical outcome; and
(ii) for every unit of increase of KBTBD 10 cDNA and/or SPINK7/ECG2 cDNA processed in step (a), said patient is expected to have a poor clinical outcome; and
(c) creating a personalized genomics profile from the data obtained.

3. The method of claim 1, comprising determining the expression level of two of said prognostic transcripts based on their corresponding cDNA processed in step (a).

4. The method of claim 1, further comprising:
(d) processing into cDNA one or more prognostic RNA transcripts selected from the group consisting of: DCD, HES6, COL6A6, PIP, SCGB 1D2, and SCGB2A2;
(e) determining the expression level of said one or more prognostic transcripts based on their corresponding cDNA processed in (d), wherein
(i) for every unit of increase of cDNA processed in step (d) corresponding to one or more of DCD, COL6A6, PEP, SCGB 1D2, and SCGB2A2, said patient is expected to have a promising clinical outcome, and
(ii) for every unit of HES6 cDNA, said patient is expected to have a poor clinical outcome and
(f) providing to the patient a recommendation for standard treatment if there is an increase in a unit of cDNA processed in step (d) corresponding to one or more of DCD, COL6A6, PEP, SCGB 1D2, and SCGB2A2, or providing to the patient a recommendation for aggressive treatment if there is an increase in a unit of HES6 cDNA processed in step (d).

5. The method of claim 1, comprising determining the expression level of all of said prognostic transcripts based on their corresponding cDNA processed in step (a).

6. The method of claim 1, wherein the patient is a mammal.

7. The method of claim 1, wherein the expression level is determined by DNA microarray analysis or real-time PCR and subsequent calculation of the mRNA copy number normalized to the amount of total tumor RNA or to the expression level of one or more housekeeping genes.

8. The method of claim 1, wherein said melanoma cells are obtained from a plantar or palmar melanoma.

9. The method of claim 2, comprising determining the expression level of two of said prognostic transcripts based on their corresponding cDNA processed in step (a).

10. The method of claim 2, further comprising processing into cDNA of one or more prognostic RNA transcripts selected from the group consisting of DCD, HES6, COL6A6, PIP, SCGB 1D2, and SCGB2A2.

11. The method of claim 2, comprising determining the expression level of all of said prognostic transcripts based on their corresponding cDNA processed in step (a).

12. The method of claim 3, further comprising:
(d) processing into cDNA one or more prognostic RNA transcripts selected from the group consisting of: DCD, HES6, COL6A6, PIP, SCGB 1D2, and SCGB2A2; and
(e) determining the expression level of said one or more prognostic RNA transcripts based on their corresponding cDNA processed in step (d), wherein
(i) for every unit of increase of cDNA processed in step (d) corresponding to one or more of DCD, COL6A6, PEP, SCGB 1D2, and SCGB2A2, said patient is expected to have a promising clinical outcome,
(ii) for every unit of increase of HES6 cDNA processed in step (d), said patient is expected to have a poor clinical outcome, and
(f) providing to the patient a recommendation for standard treatment if there is an increase in a unit of cDNA processed in step (d) corresponding to one or more of DCD, COL6A6, PEP, SCGB 1D2, and SCGB2A2, or providing to the patient a recommendation for aggressive treatment if there is an increase in a unit of HES6 cDNA processed in step (d).

13. The method of claim 3, wherein the expression level of the prognostic RNA transcripts of KBTBD10 and/or SPINK7/ECG2, and optionally of one or more genes selected from the group consisting of DCD, HES6, COL6A6, PEP, SCGB 1D2, and SCGB2A2 in said sample is determined based on their corresponding cDNA; and wherein said melanoma cells are obtained from a plantar or palmar melanoma.

14. The method of claim 4, wherein said melanoma cells are obtained from a plantar or palmar melanoma.

15. The method of claim 6, wherein the mammal is a human.

* * * * *